United States Patent

Wong et al.

[11] Patent Number: 5,514,687
[45] Date of Patent: May 7, 1996

[54] BENZOPYRIDO PIPERIDYLIDENE COMPOUNDS, COMPOSITIONS, METHODS OF MANUFACTURE AND METHOD OF USE

[75] Inventors: Jesse K. Wong, Union; John J. Piwinski, Parsippany; Michael J. Green, Skillman, all of N.J.

[73] Assignee: Schering Corporation, Kenilworth, N.J.

[21] Appl. No.: 140,210

[22] PCT Filed: Nov. 5, 1993

[86] PCT No.: US92/4003

§ 371 Date: Nov. 5, 1993

§ 102(e) Date: Nov. 5, 1993

[87] PCT Pub. No.: WO/92/20681

PCT Pub. Date: Nov. 26, 1992

Related U.S. Application Data

[63] Continuation of Ser. No. 704,534, May 23, 1991, abandoned.

[51] Int. Cl.$^6$ ............ A61K 31/44; C07D 221/00; C07D 491/044
[52] U.S. Cl. ............................................. 514/291; 546/89
[58] Field of Search .................. 546/80, 89; 514/290, 514/291

[56] References Cited

U.S. PATENT DOCUMENTS

| | | | |
|---|---|---|---|
| 3,325,501 | 6/1967 | Ettingen et al. | 514/291 |
| 3,326,924 | 6/1967 | Villani | 514/290 |
| 3,717,647 | 2/1973 | Villani | 514/290 |
| 3,803,153 | 4/1974 | Villani | 514/291 |
| 3,803,154 | 4/1974 | Drukker | 514/217 |
| 3,849,410 | 11/1974 | Nakanishi et al. | 514/253 |
| 3,966,944 | 6/1976 | Carter | 514/290 |
| 4,022,902 | 5/1977 | Remy | 514/290 |
| 4,160,031 | 7/1979 | Remy | 514/290 |
| 4,282,233 | 8/1981 | Villani | 514/290 |
| 4,355,036 | 10/1982 | Villani | 514/290 |
| 4,609,664 | 9/1986 | Hasspacher | 514/324 |
| 4,826,853 | 5/1989 | Piwinski et al. | 514/290 |
| 4,889,858 | 12/1989 | Uno et al. | 514/254 |
| 4,912,222 | 3/1990 | Griffith et al. | 546/203 |
| 5,089,496 | 2/1992 | Piwinski et al. | 514/253 |
| 5,104,876 | 4/1992 | Piwinski et al. | 514/254 |
| 5,151,423 | 9/1992 | Piwinski | 514/254 |
| 5,231,105 | 7/1993 | Shoji | 514/325 |
| 5,250,681 | 10/1993 | Shoji | 540/577 |

FOREIGN PATENT DOCUMENTS

| | | |
|---|---|---|
| 638971 | 4/1964 | Belgium . |
| 644121 | 8/1964 | Belgium . |
| 780443 | 3/1968 | Canada . |
| 0042544 | 12/1981 | European Pat. Off. . |
| 0047226 | 3/1982 | European Pat. Off. . |
| 0371805 | 6/1990 | European Pat. Off. . |
| 17764 | 4/1964 | Ireland . |
| WO88/03138 | 5/1988 | WIPO . |
| WO89/10369 | 11/1989 | WIPO . |
| WO89/10363 | 11/1989 | WIPO . |
| WO90/13548 | 11/1990 | WIPO . |
| WO92/00293 | 1/1992 | WIPO . |

OTHER PUBLICATIONS

Villani et al., Journal of Medicinal Chemistry, vol. 15, No. 7, pp. 750–754 (1972).
Arzn. Forsh., 36, 1311–1314 (1986).

*Primary Examiner*—Ceila Chang
*Attorney, Agent, or Firm*—Henry C. Jeanette

[57] ABSTRACT

Benzopyrido piperidylidene compounds of the formula

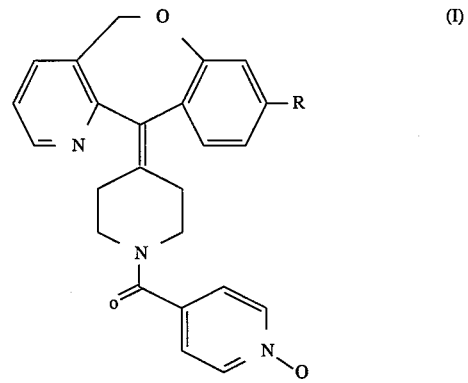

wherein R is H, Cl, Br, F or I, which are useful in treating asthma, allergy and/or inflammation.

10 Claims, No Drawings

BENZOPYRIDO PIPERIDYLIDENE COMPOUNDS, COMPOSITIONS, METHODS OF MANUFACTURE AND METHOD OF USE

This application is a 371 of PCT/US92/04003 filed May 20, 1992, which is a continuation of U.S. application Ser. No. 07/704,534, file May 23, 1991, now abandoned.

REFERENCE TO RELATED APPLICATION

This application is related to International Publication Number WO 89/10369 which published on Nov. 2, 1989 on International Application Number PCT/US89/01688 which was filed on Apr. 26, 1989 and which has priority to U.S. application Ser. No. 187,604 which was filed Apr. 28, 1988.

BACKGROUND OF THE INVENTION

International Publication Number WO 89/10369 discloses compounds of the formula:

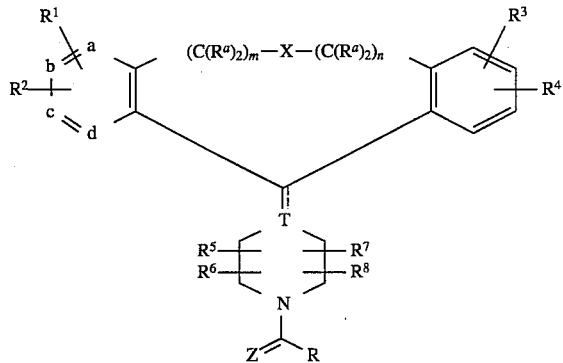

wherein:
one of a, b, c and d represents nitrogen or $-NR^{11}-$, wherein $R^{11}$ is $O^-$, $-CH_3$ or $-(CH_2)_pCO_2H$ wherein p is 1 to 3, and the remaining a, b, c and d groups are CH which may be substituted with $R^1$ or $R^2$;

$R^1$ or $R^2$ may be the same or different and each independently represents halo, $-CF_3$, $-OR^{10}$, $-C(O)R^{10}$, $-S(O)_eR^{12}$ wherein e is 0, 1, or 2, $-N(R^{10})_2$, $-NO_2$, SH, CN, $-OC(O)R^{10}$, $-CO_2R^{10}$, $-OCO_2R^{12}$, $-NR^{10}C(O)R^{10}$, alkyl, alkenyl or alkynyl, which alkyl or alkenyl groups may be substituted with halo, $-OR^{10}$ or $-CO_2R^{10}$, or $R^1$ and $R^2$ may together form a benzene ring fused to the pyridine ring;

$R^{10}$ represents H, alkyl or aryl;

$R^{12}$ represents alkyl or aryl;

$R^3$ and $R^4$ may be the same or different and each independently represents H or any of the substituents of $R^1$ and $R^2$, or $R^3$ and $R^4$ may be taken together to represent a saturated or unsaturated $C_5$ to $C_7$ ring fused to the benzene ring;

$R^5$, $R^6$, $R^7$, and $R^8$ each independently represents H, $-CF_3$, $-CO_2R^{10}$, $-C(O)R^{10}$, alkyl or aryl, which alkyl or aryl may be substituted with $-OR^{10}$, $-SR^{10}$, $-N(R^{10})_2$, $-NO_2$, $-C(O)R^{10}$, $-OC(O)R^{12}$, $-CO_2R^{10}$ and $-OPO_3(R^{10})_2$, or one of $R^5$, $R^6$, $R^7$, and $R^8$ may be taken in combination with R as defined below to represent $-(CH_2)_r$ wherein r is 1 to 4, said combination being optionally substituted with lower alkyl, lower alkoxy, $-CF_3$ or aryl, or $R^5$ may be combined with $R^6$ to represent $=O$ or $=S$, and/or $R^7$ may be combined with $R^8$ to represent $=O$ or $=S$;

T represents carbon or nitrogen, with the dotted line attached to T representing an optional double bond when T is carbon;

m and n are integers 0, 1, 2, or 3, such that the sum of m plus n equals 0 to 3;

when m plus n equals 1, X represents $-O-$, $-S(O)_e-$ wherein e is 0, 1 or 2, $-NR^{10}-$, $-C(O)NR_{10}-$, $-NR^{10}C(O)-$, $C(S)NR^{10}-$, $-NR^{10}C(S)-$, $-C(O)_2-$ or $-O_2C-$, wherein $R^{10}$ is as defined above;

when m plus n equals 2, X represents $-O-$, $-S(O)_e$ wherein e is 0, 1 or 2, or $-NR^{10}-$;

when m plus n represents 0, X can be any substituent for m plus n equalling 1 and X can also be a direct boned, cyclopropylene or propenylene;

when m plus n equals 3 then X equals a direct bond;

each $R^a$ may be the same or different, and each independently represents H, lower alkyl or phenyl;

Z represents $=O$, $=S$ or $=NR^{13}$ with $R^{13}$ equal to $R^{10}$ or $-CN$, wherein $R^{10}$ is as defined above, such that (a) when Z is O, R may be taken in combination with $R^5$, $R^6$, $R^7$ or $R^8$ as defined above, or R represents H, alkyl, aryl, $-SR^{12}$, $-N(R^{10})_2$, cycloalkyl, alkenyl, alkynyl or $-D$ wherein $-D$ represents heterocycloalkyl,

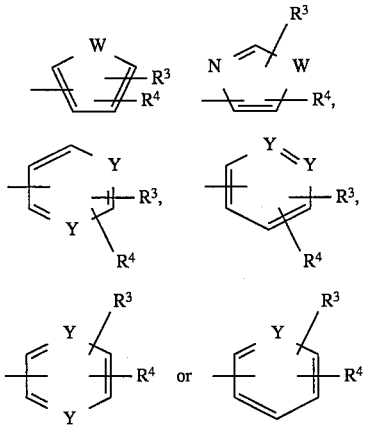

wherein $R^3$ and $R^4$ are as previously defined, and W is O, S or $NR^{10}$, and wherein Y is N or $NR^{11}$, said cycloalky, alkyl, alkenyl and alkynyl being optionally substituted with from 1–3 groups selected from halo, $-CON(R^{10})_2$, aryl, $-CO_2R^{10}$, $-OR^{14}$, $-SR^{14}$, $-N(R^{10})_2$, $-N(R^{10})CO_2R^{10}$, $-COR^{14}$, $-NO_2$ or $-D$, wherein $-D$ and $R^{10}$ are as defined above and $R^{14}$ represents $R^{10}$, $-(CH_2)_rOR^{10}$ or $-(CH_2)_qCO_2R^{10}$ wherein r is 1 to 4, q is 0 to 4; said alkeny and alkynyl R groups not containing $-OH$, $-SH$, or $-N(R^{10})_2$ on a carbon in a double or triple bond respectively; and (b) when Z represents $=S$, R represents in addition to those R groups above, aryloxy or alkoxy; and (c) where Z represents $=NR^{13}$, R represents H, alkyl, aryl, $N(R^{10})_2$, cycloalkyl, alkenyl or alkynyl.

WO 89/10369 generically discloses compounds which can have the structure:

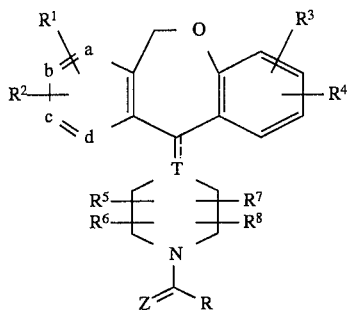

wherein Z can be O and R can be:

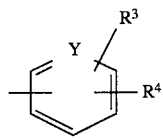

wherein Y can be $NR^{11}$ and $R^{11}$ can be $-O^-$; however, no specific compounds are disclosed with this structure.

U.S. Pat. No. 4,826,853 issued to Piwinski et al. on May 2, 1989 is the priority document for WO 88/03138 which publisehd on May 5, 1988. WO 88/03138 discloses compounds of the formula:

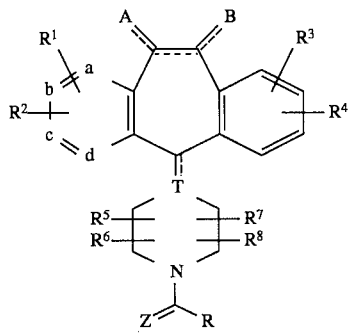

The various substituent groups are described on pages 2 to 3 of WO 88/03138. For example, X represents N or C, which C may contain an optional double bond to carbon atom 11; the dotted line between carbon atoms 5 and 6 represents an optional double bond and when no double bond is present A and B can be, amongst other groups, $H_2$; Z can be amongst other atoms, O and R can be, amongst other substituents, alkyl or

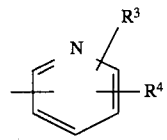

WO 90/13548 published on Nov. 15, 1990 on PCT/US90/02251 which was filed on Apr. 30, 1990 and claims priority to U.S. application Ser. No. 345,604 filed May 1, 1989 discloses compounds similar in structure to the compounds disclosed in WO 88/03138 with the difference being that the R group represents and N-oxide heterocyclic group of the formula (i), (ii), (iii), or (iv):

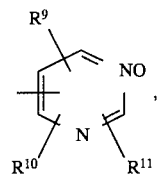

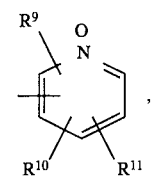

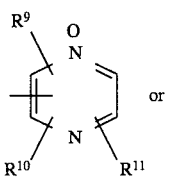

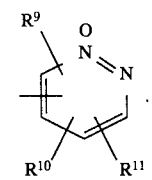

wherein $R^9$, $R^{10}$, and $R^{11}$ can be, amongst other groups, H.

Copending U.S. application Ser. No. 625,261 filed on Dec. 10, 1990 is related to WO 90/13548.

The following references have disclosed oxygen or sulfur in the bridgehead of the three ring portion of the molecule:

(1) Canadian Application 780,443, published in the name of Sandoz Patents Ltd.;

(2) Eire 17764, published Apr. 5, 1964 in the name of Sandoz Patents Ltd.;

(3) European Patent Application 81816337.6, Sandoz A.G., published Mar. 10, 1982;

(4) Belgian Application 638,971, Sandoz S.A., published Apr. 21, 1964;

(5) Belgian Application 644,121, Sandoz S.A., published Aug. 20, 1964;

(6) U.S. Pat. No. 4,609,664, issued to Hasspacher on Sep. 2, 1986;

(7) U.S. Pat. No. 3,966,944, issued to Carter on Jun. 29, 1976;

(8) U.S. Pat. No. 3,803,153, issued to Villani on Apr. 9, 1974;

(9) U.S. Pat. No. 3,803,154, issued to Drukker on Apr. 9, 1974; and

(10) U.S. Pat. No. 3,325,501, issued to Ettinsen et al. on Jun. 13, 1967.

None of references (1) to (10) above disclose substitution on the piperidylidene nitrogen similar to that described below for the compounds of this invention.

SUMMARY OF THE INVENTION

Suprisingly and unexpectedyl it has been discovered that a specific group of compounds, generically disclosed but not specifically disclosed in WO 89/10369, have a highly desireable combination of anti-PAF and anti-histamine activity. This specific group of compounds, represented by Formula I below, are in general more equipotent in their anti-PAF to anti-histamine activity then known compounds, and this activity has a longer duration.

This invention provides compounds represented by Formula I:

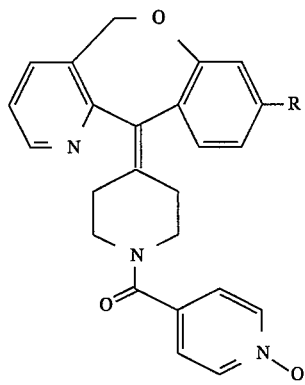

or a pharmaceutically acceptable salt or solvats thereof, wherein R represents H or a halogen atom selected from the group consisting of: Cl, Br, F, end I. Preferably R represents Cl.

Those skilled In the art will appreciate that the N-oxide heterocyclic ring may be equally represented as:

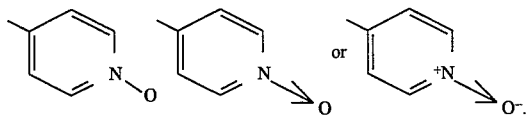

This Invention also provides a pharmaceutical composition comprising a compound represented by Formula I and a pharmaceutically acceptable carrier.

This invention further provides a method of treating asthma, allergy and/or Inflammation in a mammal, preferably a human, in need of such treatment, said method comprising administering an anti-asthmatic, anti-allergic and/or anti-inflammatory effective amount, respectively, of a compound of Formula I. Preferably the compound is administered as a pharmaceutical composition of this Invention.

DETAILED DESCRIPTION OF THE INVENTION

Certain compounds of the Invention may exist in different isomeric forms, The invention contemplates all such lagmere both in pure form and in admixture, including racemic mixtures, The compounds of the invention of Formula I can exist in unsolvated as well as solveted forms, including hydrated forms; e.g., hemlhydrate, In general, the solveted forms, with pharmaceutically acceptable solvents such as water, ethanol and the like are equivalent to the unsolvated forms for purposes of the invention.

Compounds of the invention are basic in nature, i.e., all compounds possess a pyridine ring. Hence, they may form pharmaceutically acceptable salts, e.g., acid addition salts. For example, the pyrido-nitrogen atom may form salts with strong acid. Examples of suitable acids for salt formation are hydrochloric, sulfuric, phosphoric, fumaric, maleic, methanesulfonic and other mineral and carboxylic acids well known to those in the art. The salts are prepared by contacting the free base form with a sufficient amount of the desired. acid to produce a salt in the conventional manner. The free base forms may be regenerated by treating the salt with a suitable dilute aqueous base solution such as dilute aqueous .sodium hydroxide, potassium carbonate, ammonia and sodium bicarbonate. The free base forms differ from their respective salt forms somewhat In certain physical properties, such as solubility In polar solvents, but the salts are otherwise equivalent to their respective free base forms for purposes of the invention.

All such base salts (e.g. pyridinyl nitrogen salts) are intended to be pharmaceutically acceptable salts within the scope of the invention and all acid and base salts are considered eqivalent to the free forms of the corresponding compounds for purposes of the invention.

The following processes may be employed to produce compounds of Formula I.

Processes A to C For The Preparation Of Compounds Of Formula I

Process A

In the preferred method, a compound of Formula II (wherein R is as defined in Formula I) can be coupled with isonicotinic acid N-oxide in the presence of a coupling agent such as 1-(3-dimethylaminopropyl)-3-ethyl carbodiimide hydrochloride (DEC), N,N'-dicyclohexylcarbodiimide (DCC) or N,N'-carbonyl-diimidazole (CDI) to produce compounds of Formula I:

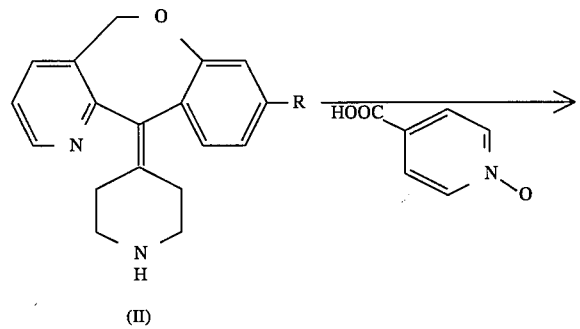

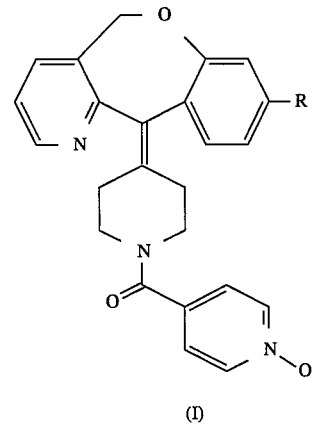

The reaction is usually conducted in an inert solvent such as tetrahydrofuran or methylene chloride at a temperature between 0° C. and reflux, usually at room temperature. When the coupling agent is DCC or DEC, the reaction Is preferably run In the presence of 1-hydroxybenzotriazole (HOBT).

Process B

A compound of Formula II may also be reacted with a compound of Formula III in the presence of a base to produce compounds Formula I:

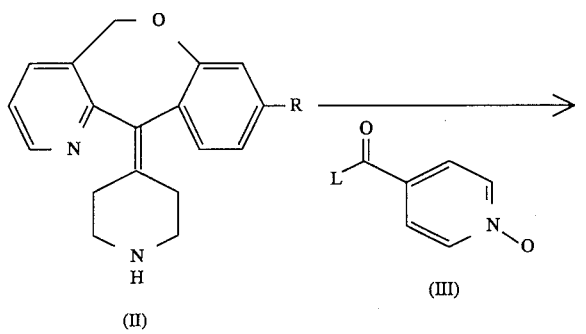

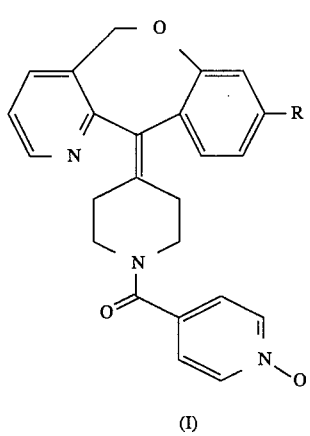

Representative examples of bases are pyridine and triethylamine. L designates a suitable leaving group. For example, a compound of Formula III may be an acyl halide (e.g., L is Cl), in which case compound III can be generated from the corresponding carboxylic acid using oxalyl chloride.

Process C

Compounds of Formula I may also be prepared by reacting a compound of Formula IV with a compound of Formula III;

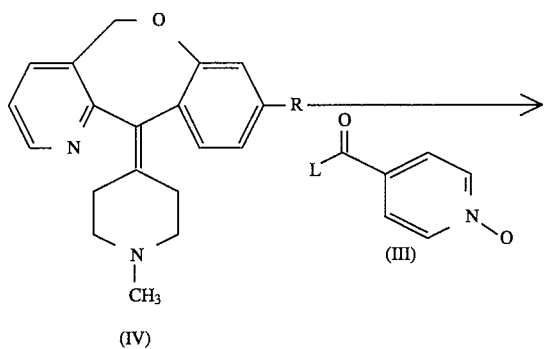

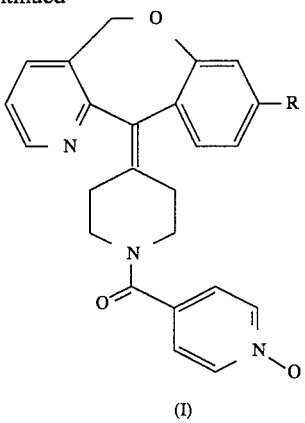

Preferably this reaction may be run in the presence of a suitable nucleophile (e.g., LiI, and the like) in an inert solvent (e.g., toluene, dioxane or xylenes). A suitable base, such as triethylamine may be added, and heating may usually be required. Typically, a temperature ranging from about 50° to about 150° C. (preferably about 100° to about 120° C.) may be utilized depending on the boiling point of the solvent.

Preparation Of Intermediate Compounds Used To Prepare Compounds of Formula I By Above Processes A To C

Preparation of a compound of Formula II

Compounds of the general Formula II can be prepared by cleaving a carbamate group (COOR" wherein R" is an alkyl group, such as ethyl, or an aryl group, such as phenyl) from the corresponding carbamates of Formula V. This can be accomplised by a variety of methods including acid hydrolisis (e.g., HCl) or base hydrolysis (e.g., KOH) as long as R" is a group which does not prevent the cleavage reaction (e.g., R" can be an alkyl group such as methyl or ethyl). Alternatively, depending on the nature of R", as determined by one who is skilled in the art, a compound of Formula V may be treated with an organometalic reagent (e.g., Ch₃Li wherein R" is an alkyl group such as ethyl) or a reductive reagent (e.g., Zn in acid where R" is 2,2,2-trichloroethyl) in order to produce a compound of Formula II.

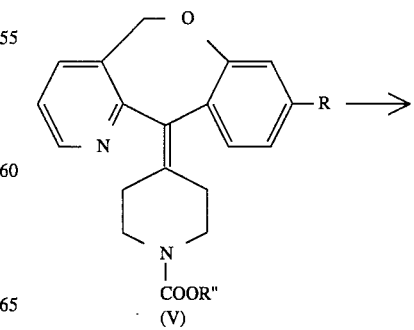

9

-continued

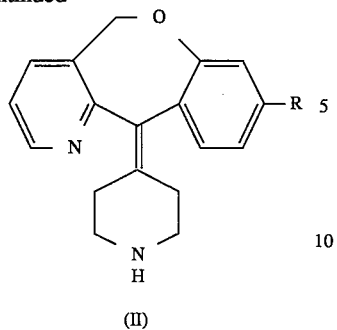

(II)

Preparation of a compound of Formula V

Compounds of Formula V can be prepared from the corresponding N-methly compounds of Formula IV by treating compounds of Formula IV with a suitable chlorocarbamate containing R" (e.g., ClCOOR"). The reaction can usually be carried out at an elevated temperature (e.g., about 70° to about 100° C.) by heating a compound of Formula IV in an inert solvent, such as toluene, in the presence of the chlorocarbamate and optionally with a base such as triethylamine. This procedure is described for similar compounds in U.S. Pat. No. 4,282,233 and 4,335,036, the disclosures of each being incorporated herein by reference thereto.

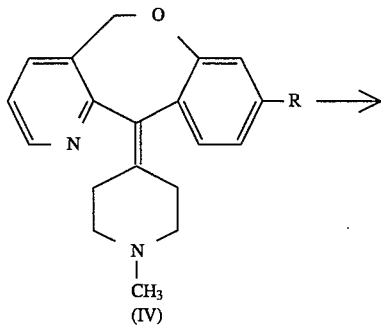

(IV)

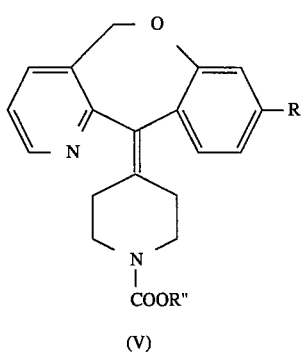

(V)

10

Preparation of a compound of Formula VI and VII

Preparation of a compound of Formula II from compounds of Formula VI and VII Those skilled in the art will appreciate that there are other methods for converting a compound of Formula IV to a compound of Formula II. For example, treatment of a compound of Formula IV with phosgene to produce a compound of the Formula VI followed by hydrolysis with aqueous acid may produce compounds of Formula II. Alternatively, treatment of a compound of Formula IV with cyanogen bromide (i.e., BrCN) via Von Braun reaction conditions would provide a nitrile of Formula VII as illustrated below. Subsequent hydrolysis of the nitrile of Formula VII under either aqueous basic or aqueous acidic conditions would produce a compound of Formula II.

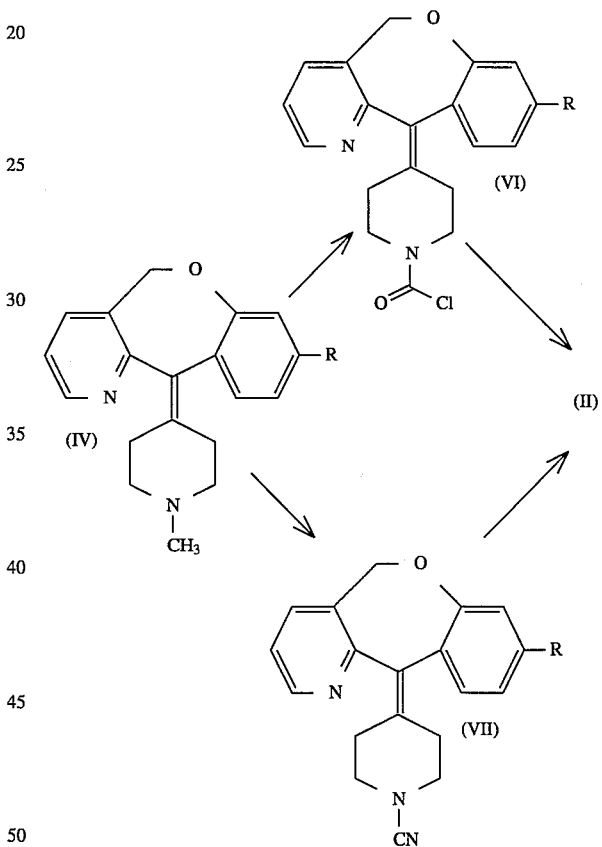

Preparation of compounds of Formula IV, method 1 steps (a)–(e)

(a) Compounds of Formula IV can be prepared from a corresponding alcohol of Formula VIII by using either acidic or basic conditions in accordance with methods well known in the art. For example, treatment of a compound of Formula VIII with trifluoromethanesulfonic acid and heating (about 40° to about 60° C.) the mixture results in dehydration of the alcohol to produce the olefin of Formula IV. Other acids such as polyphosphoric acid or sulfuric acid may also be employed.

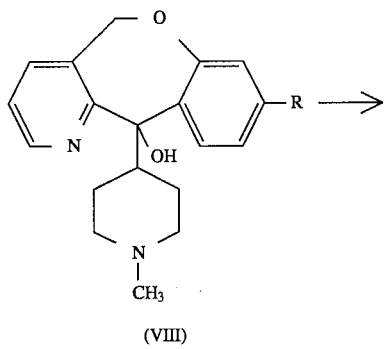

(VIII)

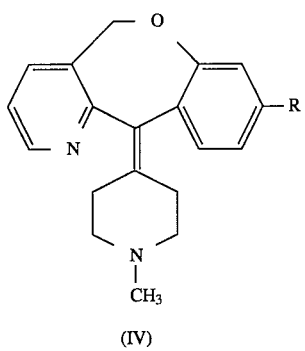

(IV)

(b) The alcohol of Formula VIII can be prepared via the treatment of a ketone of Formula IX with the Grignard reagent derived from N-methyl-4-chloropipiridine in an inert solvent such as tetrhydrofuran. Other organsmetallic reagents known in the art may also be used; for example, N-methyl-4-lithiopiperidine. The reaction may be conducted at or below room temperature (e.g., about −15° to about 25° C.); however, the reaction mixture may be refluxed if necessary. Quenching the reaction with a mild acid (such as aqueous hydrochloric acid) or water produces an alcohol of Formula VIII. The Grignard reagent may be prepared from the corresponding halo derivative using methods well known in the art.

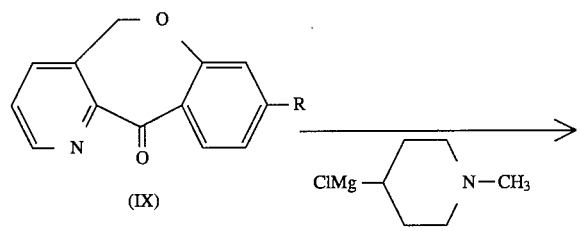

(IX)

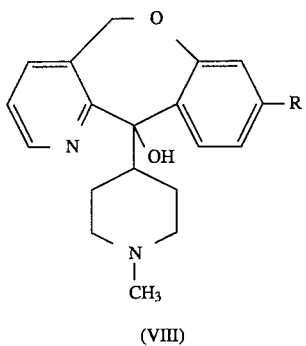

(VIII)

(c) There are many methods known in the art that may be employed for the preparation of substituted kotenos of Formula IX. For example, the ketones of Formula IX can be prepared via an intramolecular cyclization of the corresponding nitrile of Formula X. This transformation may be accomplished using a strong acid, such as trifluoromethanesulfonic acid, at room temperature. Other temperatures may be employed, for example about −15° to about 100° C. Other acids which may be used include sulfuric acid or polyphosphoric acid. The addition of water or aqueous acid to the reaction mixture is necessary following the cyclization in order to effect hydrolysis of the resultant imine to the corresponding ketone of Formula IX. Alternatively, an Intramoleculer Friedel-Crafts acylation of the acid chloride of Formula XI would also provide the deslrecl ketone of Formula IX. The reaction may be carried out under usual Friedel-Crafts conditions in an inert solvent and in the presence of a Lewis acid such as aluminum chloride. The necessary acid chloride of Formula XI may be obtained from the nitrile of Formula X by the nitrile's hydrolysis to the corresponding carboxylic acid with aqueous acid (e.g., aqueous hydrochloric add with heating) followed by its conversion to the acid chloride of Formula XI by standard conditions (e.g., thlonyl chloride or oxalyl chloride) well known to those skilled in the art.

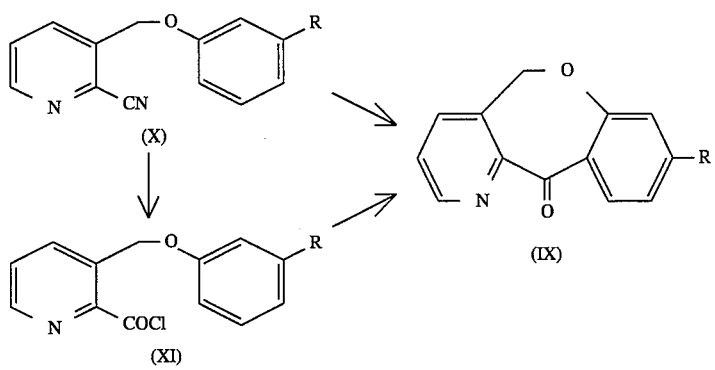

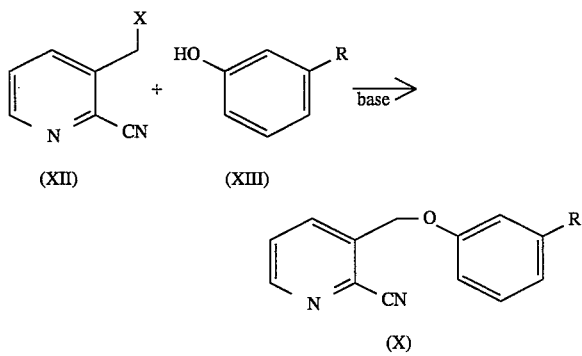

(d) Compounds of Formula X can generally be prepared by reaction of an alkyl halide of Formula XII (wherein X is a halogen or other leaving group known in the art) with a phenol of Formula XIII. Those skilled In the art will appreciate that these displacements may be conducted at a variety of temperatures (usually between room temperature and 100° C.) In the presence of a base and a suitable polar solvent. Representative examples of bases which may be used to remove the phenolic proton include cesium carbonate (wherein acetone may be used as the polar solvere) or sodium hydride (wherein tetrahydrofuran may be used as the polar solvent). In this method, the alkyl halide of Formula XII may be coupled to the phenol of Formula XIII to produce the nitdie of Formula X.

Alternatively, if X is a hydroxyl group in the compound of Formula XII then it may be coupled with the phenol of Formula XIII using known in the art Mitsunobe conditions. For example, the compounds of Formulas XII and XIII may be coupled to produce a compound of Formula X using trlphenyl phosphine and diethyl azadicarboxylate in and inert dry solvent such as tetrehydrofuran. The reaction may usually be conducted at or below 0° C. (e.g., about −15° to about 0° C.); however, the reaction may also be heated to reflux.

(e) The required alkyl halide of Formula XII (X is halogen) can be obtained from the corresponding 3-methyl-2-cyanopyridine of Formula XIV. Halogenation of the compound of Formula XIV can best be accomplished under free radical conditions using, for example, N-bromosuccinamide to provide the bromide (X=Br), or sulfuryl chloride to provide the chloride (X=Cl). These reactions are carried out in an inert solvent, such as carbon tetrachloride, either in the presence of an initiator, such as aza(bis)isobutyronitrile (ABIN), and heat (about >50° C.) or light. Alternatively, a compound of Formula XII, wherein X is a hydroxyl group, may be obtained from the corresponding carboxylic acid of Formula XV using reductive conditions which do not result in reduction of the cyano group (e.g., diborane in tetrahydrofuran) as is well known in the art,

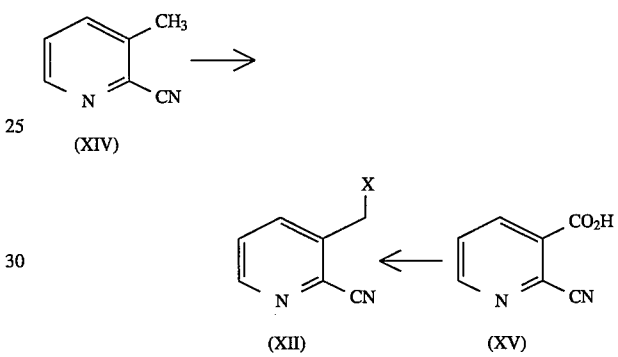

In the above processes, it is sometimes desirable and/or necessary to protect certain groups during the reactions. Conventional protecting groups are operable as described in Greene, T. W., "Protective Groups In Organic Synthesis," John Wiley & Sons, New York, 1981, the disclosure of which is incorporated herein by reference thereto. After the reaction or reactions, the protecting groups may be removed by standard procedures.

The compounds of the invention possess platelet-activating factor ("PAF") and histamine antagonistic properties. The compounds of the invention are, therefore, useful when PAF and/or histamine are factors in the disease or disorder. This includes allergic diseases such as asthma, respiratory distress syndrome, urticaria and inflammatory diseases such as rheumatiod arthritis and osteo-arthritis. For example, PAF is an important mediator of such processes es platelt aggregation, smooth muscle contraction (especially In lung tissue), vascular permeability and neutrophil activation. Recent evidence implicates PAF as an underlying factor involved in airway hyperreactivity, The PAF antagonistic properties of these compounds may be demonstrated by use of standard pharmacological testing procedures as described below. These test procedures are standard tests used to determine PAF antagonistic activity and to evaluate the usefulness of said compounds for counteracting the biological effects of PAF, The in vitro assay is a simple screening test, while the in vivo test mimics clinical use of PAF antagonists to provide data which simulates clinical use of the compounds described herein.

A. IN VITRO STUDIES

Platelet Aggregation Assay

Platelet-activating factor (PAF) causes aggregation of platelets by a receptor-mediated mechanism. Therefore, PAF-induced platelet aggregation provides a simple and convenient assay to screen compounds for PAF antagonism.

Human blood (50 mL) was collected from healthy male donors in an anticoagulant solution (5 mL) containing sodium citrate (3.8%) and dextrose (2%), Blood was centrifuged at 110×g for 15 min. and the supeernatant platelet-rich plasma (PRP) carefully transferred into a polypropylene tube. Platelet-poor-plasma (PPP) was prepared by centrifuging PRP at 12,000×g for 2 min. (Beckman Microfuge B). PRP was used within 3 hr. of drawing the blood.

PAF was dissolved In chloroform:methanol (1:1, v/v) at a concentration of 2 mg/mL and stored at −70° C. An aliquot of this solution was transferred to a polypropylene tube and dried under a flow of nitrogen gas. To the dried sample was added Hepes-e-BSA (BSA= bovine serum albumen) buffer (25 mM Hepes, pH 7.4, 1254 mM NaCl, 0.7 mM $MgCl_2$ and 0.1% BSA) to obtain a 1 mM solution and sonicated for 5 min. in a bath sonicator. This stock solution was further diluted to appropriate concentrations in Hepes-saline-BSA buffer. Collagen (Sigma) and adenosine diphosphate (ADP) (Sigma) were purchased as solutions. Test compounds were initially dissolved in dimethyl sulfoxide (DMSO) at a concentration of 50 mM and then further diluted in Hepes-saline-BSA buffer to achieve appropriate concentrations.

When an aggregating agen such as PAF is added to PRP, platelets aggregate. An aggregometer quantifies this aggreation by measuring and comparing light (infra-red) transmission through PPP and PRP. Aggregation assays were performed using a dual-channel aggregometer (Model 440, Chrono-Log Corp., Havertown, Pa.). PRP (0.45 mL) in aggregometer cuvettes was continually stirred (37° C.). Solution (50 μL) of test compounds or vehicle were added to the PRP and, after incubation for 2 min., 10–15 μl aliquots of PAF solution were added to achieve a final concentration of $1-5 \times 10^{-8}$M. In different experiments the aggregatory response was kept within a set limit by varying the concentration of PAF. Incubations were continued until the increase in light transmission reached a maximum (usually 2 min.). This increase in lighyt transmission reflecting platlet aggregation is transmitted to a computer by the Chrono-Log model 810 AGGRO/LINK interface. The AGGRO/LINK calculates the slope of transmission change, thus providing the rate of aggregation. Values for inhibition were calculated by comparing rates of aggregation obtained in the absence and the presence of the compound. For each experiment, a standard PAF antagonist such as 8-chloro-6,11-dihydro-11-(1-acetyl-4-piperidylidene)- 5H-benzo[5,6]cyclohepta[1,2-b]pyridine was used as a positive control.

Compounds that inhibit PAF-induced aggregation were tested against several other aggregating agents including collagen (0.2 mg/mL) and ADP (2 μM). Compounds showing no activity against these latter agents were considered to be specific PAF antagonists. Results are shown in TABLE 1 below.

B. In Vivo Studies: Agonist-Induced Responses
Spasmogen-Induced Bronchospasm in Guinea Pigs Male Hartley guinea pigs (450–550 g) were obtained from Charles River Breeding Laboratories. The animals were fasted overnight and the following day were anesthetized with 0.9 mL/kg i.p. of dialurethane (containing 0.1 g/mL dialylbarbiturikc acid, 0.4 g/mL ethylurea and 0.4 g/mL urethane). The left jugular vein was cannulated for the administration of compounds. The trachea was cannulated and the animals were venticlated by a rodent respirator at 55 strokes/min. with a stroke volume of 4 mL. A side arm to the tracheal cannula was connected to a pressure transducer to obtain a continuous measure of inflation pressure. Bronchoconstriction was measured as the percent increase in inflation pressure that peaked within 5 min. after challenge with spasmogen. The animals were challenged i.v. with either histamine (10 ug/kg) or PAF (0.4 μg/kg in isotonic saline containing 0.25% BSA). Each animal was challenged with only a single spasmogen. The effect of a compound on the bronchospasm is expressed as a percent inhibition of the increase in inflation pressure compared to the increase in a control group. Results are shown in Table 1 below.

In Table 1 the column "No." represents "Compound Numbers" and Compound Numbers 1 to 4 in Table 1 refer to:

(a) Compound No. 1 is disclosed in WO 88/03138, discussed above, and has the structure:

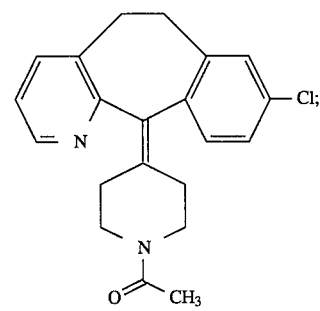

(b) Compound No. 2 is disclosed in WO 89/10369, discussed above, and has the structure:

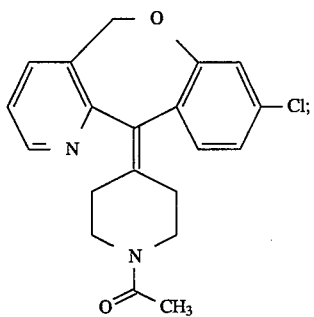

(c) Compound No. 3 is disclosed in WO 90/13548, discussed above, and has the structure:

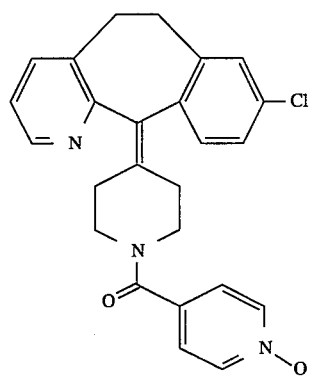

; and (d) Compound No. 4, a compound of the invention, has the structure;

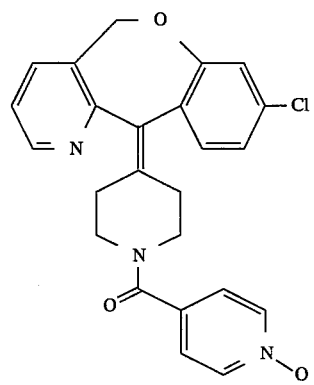

TABLE 1

| No. | PAF Antagonism (in vitro) IC$_{50}$ (μM) | Agonist Bronchospasm (in vivo)-Oral | | | |
|---|---|---|---|---|---|
| | | PAF | | Histamine | |
| | | Dose (mg/kg) | Inhibition (%) | Dose (mg/kg) | Inhibition (%) |
| 1 | 0.6 | 3 | 3[a] | 3 | 49[a] |
| | | 15 | 32[b] | 15 | 100[b] |
| 2 | 6 | 10 | 27[a] | — | — |
| 3 | 0.2 | 3 | 93[a] | 3 | 37[a] |
| | | 5 | 12[b] | 5 | 33[b] |
| | | 15 | 13[d] | 15 | 64[d] |

TABLE 1-continued

| No. | PAF Antagonism (in vitro) IC$_{50}$ (μM) | Agonist Bronchospasm (in vivo)-Oral | | | |
|---|---|---|---|---|---|
| | | PAF | | Histamine | |
| | | Dose (mg/kg) | Inhibition (%) | Dose (mg/kg) | Inhibition (%) |
| 4 | 0.4 | 3 | 76[a] | 3 | 46[a] |
| | | 10 | 94[c] | 10 | 73[c] |
| | | 10 | 55[d] | 10 | 95[d] |

[a]% inhibition 2 hours after drug
[b]% inhibition 8 hours after drug
[c]% inhibition 6 hours after drug
[d]% inhibition 16 hours after drug The data in Table 1 demonstrate that the compounds of this invention (e.g., Compound No. 4 in Table 1):

(1) have activity as antagonists of PAF and histamine;
(2) have anti-PAF and anti-histamine activities that are more equipotent than compounds known in the art as dual antagonists of PAF and histamine; and
(3) have a longer duration of the anti-PAF activity than compounds known in the art as dual antagonists of PAF and histamine.

Thus, the compounds of this invention are more equipotent and have a longer lasting (longer duration) activity as antagonists of PAF and histamine then compounds known in the art as dual antagonists of PAF and histamine.

For preparing pharmaceutical composition from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 70 percent active ingredient. Suitable solid carriers are known in the art, e.g. magnesium carbonate, magnesium stearate, talc, sugar, lactose. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example there may be mentioned water or water-propylene glycol solutions for parenteral injection.

Liquid form preparations may also include solutions for intranasal administration.

Aerosol preparations suitable for inhalation may include solutions and solids in powder form, which may be in combination with a pharmaceutically acceptable carrier, such as an inert compressed gas.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administer orally.

Preferably, the pharmaceutical preparation is in unit dosage form. In such form, the preparation is subdivide into unit doses containing appropriate quantities of the active component, e.g., an effective amount to achieve the desired purpose.

The quantity of active compound in a unit dose of preparation may be varied or adjusted from about 0.1 mg to 1000 mg, more preferably from about 1 mg. to 500 mg, according to the particular application. The appropriate dosage can be determined by comparing the activity of the compound with the activity of a known antihistaminic compound such as 8-chloro-6,11-dihydro-11-(1-ethoxycarbonyl-4 -piperidylidene)-5H-benzo[5,6]cyclohepta[1,2-b] pyridine, which compound is disclosed in U.S. Pat. No. 4,282,233.

The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The amount and frequency of administration of the compounds of the invention and the pharmaceutically acceptable salts therof will be regulated according to the judgement of the attending clinician considering such factors as age, condition and size of the patient as well as severity of the symptyoms being treated. A typical recommended dosage regimen is oral administration of from 10 mg to 1500 mg/day, preferably 10 to 750 mg/day, in two to four divided doses to achieve relief of the symptoms. The compounds are non-toxic when administered within this dosage range.

The following examples are intended to illustrate, but not to limit, the present invention.

PREPARATIVE EXAMPLE

A. 2-Cyano-3-(bromomethyl)pyridine

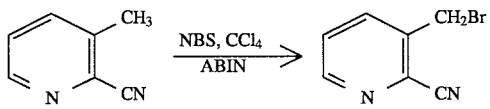

Combine 2-cyano-3-methylpyridine (11.8 g), N-bromosuccinimide (NBS) (26.8 g, 1.5 eq.) and aza(bis)isobutyronitrile (ABIN) (180 mg) in dry $CCl_4$ (300 mL). Reflux the mixture overnight.

Pour the mixture into water, basify with NaOH and extract with $CH_2Cl_2$. Wash the organic portion with water, dry ($Na_2SO_4$), filter and concentrate to obtain a liquid. Chromatograph the product, eluting with 30% diethyl ether in hexanes. Combine the appropriate fractions to obtain the mono bromo compound (5.01 g) as a yellowish solid: m.p. 41.5°–42.5° C.

B. 2-Cyano-3-(3-Chlorophenoxymethyl)pyridine

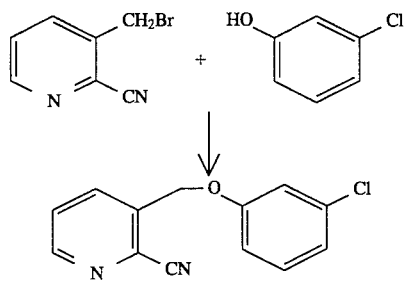

Stir a solution of the title compound of part A above (0.71 g, 3.6 mmol), NaI (54 mg, 0.1 eq) and $Cs_2CO_3$ (1.17 g, 1.0 eq) in dry acetone (17 mL, dried over $MgSO_4$) at room temperature for 5 minutes, then add 3-chlorophenol (463 mg) via a syringe.

Reflux over an oil bath for 4.5 hours.

Filter and wash the filtrate with dry acetone. Concentrate the filtrate, suspend in diethyl ether, and refilter to obtain a brown solid which is the title compound in crude form. Triurate with pentane, and resuspend in diisopropyl ether (40 mL) with charcoal, and heat on a steam bath.

Filter and evaporate the solvent to obtain the title compound, which crystallizes to form a white solid (640 mg): m.p. 70°–72° C.

C. 8-Chloro-5,11-dihydro[1]benzoxepino[4,3-b]pyridin-11-one

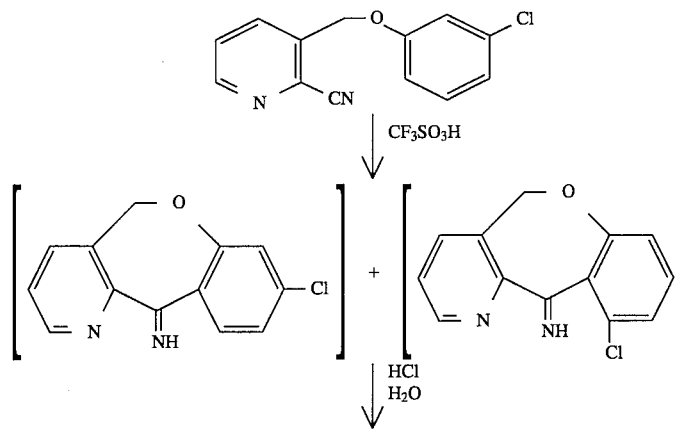

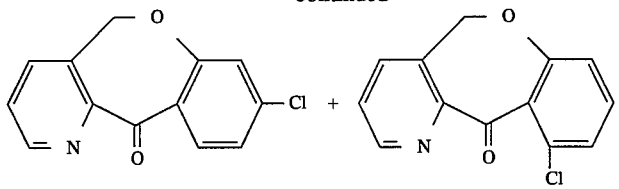

Stir the title compound from part B above (6.1 g) in CF₃SO₃H (60 mL) at room temperature for 3 hours. Upon completion, quench with H₂O and conc. HCl (30%) and continue stirring for 0.5 hours.

Warm to 35° C. for 0.5 hours. Basify with NaOH (25%) and extract with CH₂Cl₂ (2×). Wash with brine (2×), filter and dry over Na₂SO₄, and concentrate in vacuo to afford a semi-solid.

Triturate the resulting semisolid (6.35 g) with diisopropyl ether and separate the isomers via flash chromatography (30% ethyl acetate in hexanes). Combine the appropriate fractions to obtain the title compound as a solid (4.902 g): m.p. 139.5°–140.5° C., and the 10-chloro compound as a solid (498 mg): m.p. 100°–102° C.

D.
1-Methyl-4-(8-chloro-11-hydroxy-5,11-dihydro[1]benzoxepino[4,3-b]pyridinyl)piperidine

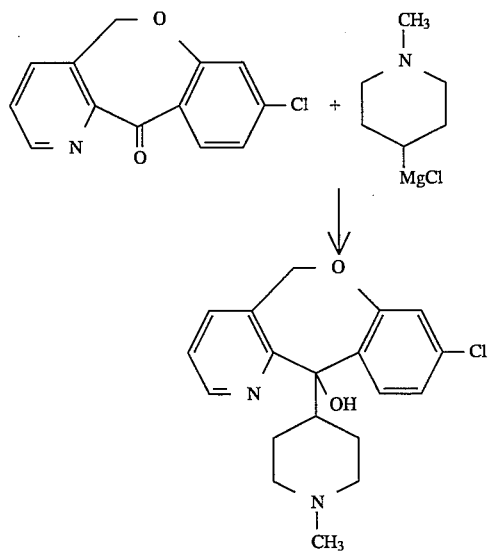

Slowly add the Grignard reagent (11.9 mL, 1.2M) derived from N-methyl-4-chloropiperidine to a stirred solution of the title compound from part C above (3.47 g) in dry tetrahydrofuran (37 mL). Stir the solution for 30 minutes after the addition.

Quench the reaction with ice and NH₄Cl. Extract the solution with CH₂Cl₂ (2×), dry, filter and concentrate to obtain the title compound. Chromatograph the product on silica gel eluting with 5→7.5% CH₃OH/NH₃ in CH₂Cl₂ to obtain the title compound as a glass (2.56 g): MS (EI) m/e 344 (M⁺).

E.
1-Methyl-4-(8-chloro-5,11-dihydro[1]benzoxepin[4,3-b]pyridin-11-ylidene) piperidine

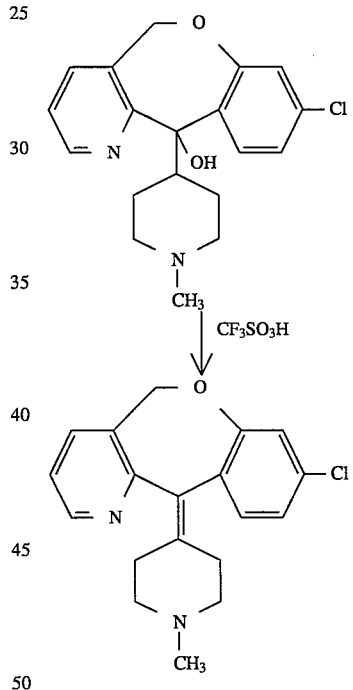

Stir the title compound from part D above (934 mg) in CF₃SO₃H (20 mL) at room temperature for 15 minutes. Raise temperature to 45° C. on an oil bath and maintain for 1.25 hours. Cool to room temperature and pour the mixture into ice water. Basify with dilute NaOH, and extract with CH₂Cl₂ (2×). Wash with brine (1×) and dry over Na₂SO₄ to obtain the title compound as a brown glass.

Purify by combining with charcoal in ethyl acetate, then filter and remove solvent to obtain a yellowish brown solid.

Recrystallize from ethyl acetate and diisopropyl ether to obtain the title compound as an off-white solid (540 mg): m.p. 168°–170° C.

23

F. 1-Ethoxycarbonyl-4-(8-chloro-5,11-dihydro[1]benzoxepino[4,3-b]pyridin-11-ylidene)piperidine

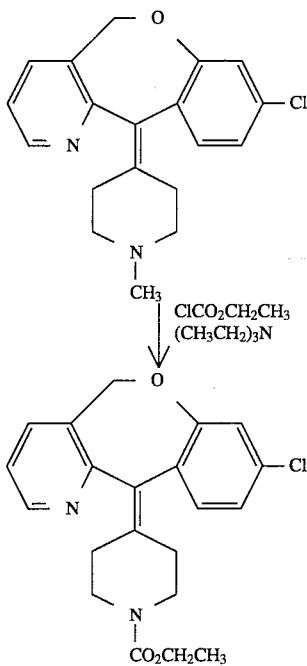

Dissolve the title compound from part E above (474 mg, 1.45 mmol in toluene (10 mL) and add triethylamine (0.656 mL). Warm and maintain the reaction at 80°–85° C. and slowly add ethyl chloroformate (1.242 mL). Maintain the reaction at 80°–85° C. while stirring for 3 hours.

Quench the reaction with H₂O and extract with ethyl acetate (2×100 mL). Wash with brine, separate and dry over Na₂SO₄. Remove the solvent and purifyl via flash chromatograph, eluting with 40→60% ethyl acetate in hexanes to yield the title compound as an off-white solid, which may be purified by trituration with pentane and diisopropyl ether to render a powder (428 mg): m.p. 118°–120° C.

G. 4-(8-Chloro-5,11-dihydro[1] benzoxepino[4,3-b]pyridin-11-ylidene)piperidine

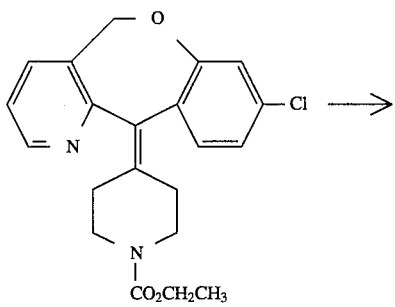

24

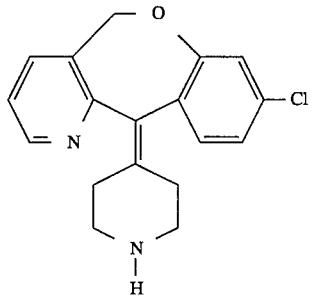

Dissolve the title compound from part F above (333.8 mg) in ethanol (5 mL) and add 14% aqueous KOH. Reflux under an argon atmosphere for 19 hours.

Quench the reaction with H₂O and extract with CH₂Cl₂ (3× 100 mL). Wash with brine (1×100 mL), dry over Na₂SO₄ and filter. Remove the solvent to yield a glassy off-white solid.

Recrystallize with ethyl acetate/diisopropyl ether to yield the title compound as a white powder (161.5 mg): m.p. 166°–176° C. (dec).

EXAMPLE 1

4-(8-Chloro-5,11-dihydro[1]benzoxepino[4,3-b]pyridin-11-ylidene)-1-(4-pyridinylcarbonyl)piperidine N¹-oxide

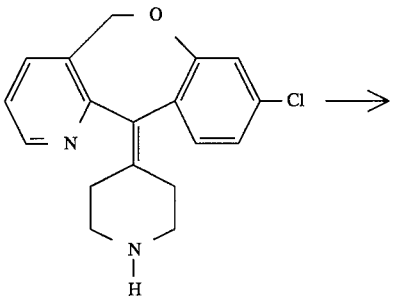

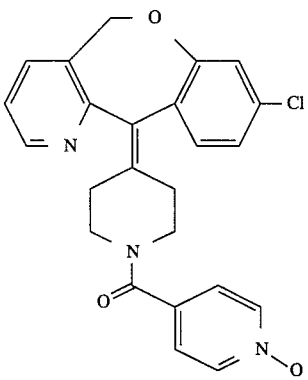

Add isonicotinic acid N-oxide (0.90 g, 6.47 mmole) to 8-chloro-5,11-dihydro-11(4-piperidinylidene)[1] benzoxepino-[4,3-b]pyridine (1.19 g, 3.80 mmole) in dichloromethane (25 mL) at 0° C. under a nitrogen atmosphere. Add 1-hydroxybenzotriazole hydrate (0.87 g, 6.47 mmole)

and 1-(3-dimethylaminopropyl)-3-ethylcarbodiimide hydrochloride (1.24 g, 6.47 mmole). Warm the reaction mixture up slowly, and stir for 22 hours at room temperature. Add 1N NaOH (40 mL), and separate layers. Extract the aqueous portion with dichloromethane (2×40 mL). Wash the combined organic portions with saturated NaCl, dry with $MgSO_4$, filter, and concentrate in vacuo. Dissolve the foamy solid in dichloromethane, and chromatograph on silica gel, eluting with 7% methanol in dichloromethane, then 10% methanol in dichloromethane. Combine the appropriate fractions, and concentrate under reduced pressure to give a beige foamy solid. Dissolve the solid in ethanol, and add 1.1 equivalents of 20 wt % HCl in ethanol. Rotoevaporate to remove the solvent. Dry the product (1.50 g) at room temperature under high vacuum (0.05 torr) for 16 hours to obtain the title compound as a tan powder, containing ¾ mole ethanol and ¼ mole water, with a melting range of 194°–200° C.

The following are examples of pharmaceutical dosage forms which may contain a compound of the invention. As used herein, the term "active compound" is used to designate the compound 4-(8-Chloro-5,11-dihydro[1]benzoxepino[4,3-b]pyridin-11-ylidene)-1-(4-pyridinylcarbonyl)piperidine $N^1$-oxide. The scope of the invention in its pharmaceutical composition aspect is not to be limited by the examples provided, since any other compound of structural Formula I can be substituted into the pharmaceutical composition examples.

Pharmaceutical Dosage Form Examples

Example A

Tablets

| No. | Ingredient | mg/tablet | mg/tablet |
|---|---|---|---|
| 1 | Active Compound | 100 | 500 |
| 2 | Lactose USP | 122 | 113 |
| 3 | Corn Starch, Food Grade, as a 10% paste in Purified Water | 30 | 40 |
| 4 | Corn Starch, Food Grade | 45 | 40 |
| 5 | Magnesium Stearate | 3 | 7 |
|   | TOTAL | 300 | 700 |

Method of Manufacture

Mix Item Nos. 1 and 2 in a suitable mixer for 10–15 minutes. Granulate the mixture with Item No. 3. Mill the damp granules through a coarse screen (e.g., ¼") if needed. Dry the damp granules. Screen the dried granules if needed and mix with Item No. 4 and mix for 10–15 minutes. Add Item No. 5 and mix for 1–3 minutes. Compress the mixture to appropriate size and weight on a suitable tablet machine.

Example B

Capsules

| No. | Ingredient | mg/tablet | mg/tablet |
|---|---|---|---|
| 1 | Active Compound | 100 | 500 |
| 2 | Lactose USP | 106 | 123 |
| 3 | Corn Starch, Food Grade | 40 | 70 |
| 4 | Magnesium Stearate NF | 4 | 7 |
|   | TOTAL | 250 | 700 |

Method of Manufacture

Mix Item Nos. 1, 2, and 3 in a suitable blender for 10–15 minutes. Add Item No. 4 and mix for 1–3 minutes. Fill the mixture into suitable two-piece hard gelatin capsules on a suitable encapsulating machine.

While the present invention has been described in connection with certain specific embodiments thereof, it will be evident to one of ordinary skill in the art that many alternatives, modifications and variations may be made. All such alternatives, modifications and variations are intended to be included within the spirit and scope of the invention.

What is claimed is:

1. A compound of Formula I:

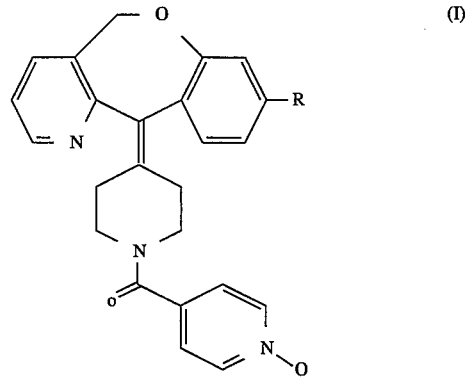

or a pharmaceutically acceptable salt or solvate thereof, wherein R is selected from the group consisting of: H and halogen atoms, said halogen atoms being selected from the group consisting of: Cl, Br, F, and I.

2. A compound of the formula:

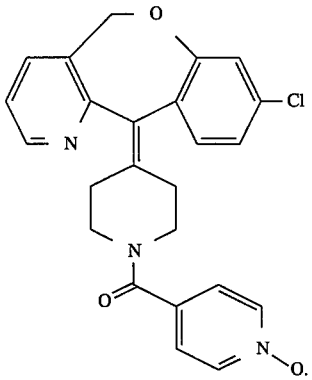

3. A pharmaceutical composition comprising a compound of claim 1 in combination with a pharmaceutically acceptable carrier.

4. A method of treating asthma comprising administering to a mammal in need of such treatment an anti-asthmatic effective amount of a compound of claim 1.

5. A method of treating allergy comprising administering to a mammal in need of such treatment an anti-allergic effective amount of a compound of claim 1.

6. A method of treating inflammation comprising administering to a mammal in need of such treatment an anti-inflammatory effective amount of a compound of claim 1.

7. A pharmaceutical composition comprising a compound of claim 2 in combination with a pharmaceutically acceptable carrier.

8. A method of treating asthma comprising administering to a mammal in need of such treatment an anti-asthmatic effective amount of a compound of claim 2.

9. A method of treating allergy comprising administering to a mammal in need of such treatment an anti-allergic effective amount of a compound of claim 2.

10. A method of treating inflammation comprising administering to a mammal in need of such treatment an anti-inflammatory effective amount of a compound of claim 2.

* * * * *